United States Patent
Portolan et al.

(10) Patent No.: US 10,478,393 B2
(45) Date of Patent: Nov. 19, 2019

(54) METHOD OF COSMETIC TREATMENT TO PROTECT THE SKIN FROM POLLUTION AND IMPROVE SKIN REGENERATION

(71) Applicants: ISP Investments LLC, Wilmington, DE (US); ELC Management LLC, Melville, NY (US)

(72) Inventors: Frédérique Portolan, Valbonne (FR); Jean-Marie Botto, Valbonne (FR); Joel Mantelin, Cannes (FR); Isabelle Imbert, Cannes (FR); Nouha Domloge, Opio (FR); Daniel B. Yarosh, Merrick, NY (US); Nevena Jurukovska-Karaman, Stony Brook, NY (US); Nadine A. Perdonet, Huntington Station, NY (US); Kelly Dong, Merrick, NY (US); Edward Pelle, Valley Steam, NY (US)

(73) Assignees: ISP Investments LLC, Wimington, DE (US); ELC Management LLC, Melville, NY (US)

( * ) Notice: Subject to any disclaimer, the term of this patent is extended or adjusted under 35 U.S.C. 154(b) by 0 days.

(21) Appl. No.: 15/564,806

(22) PCT Filed: Mar. 30, 2016

(86) PCT No.: PCT/US2016/024833
§ 371 (c)(1),
(2) Date: Oct. 6, 2017

(87) PCT Pub. No.: WO2016/164216
PCT Pub. Date: Oct. 13, 2016

(65) Prior Publication Data
US 2018/0104178 A1    Apr. 19, 2018

Related U.S. Application Data

(60) Provisional application No. 62/145,362, filed on Apr. 9, 2015.

(51) Int. Cl.
| | | |
|---|---|---|
| *A61K 36/87* | (2006.01) | |
| *A61K 8/9794* | (2017.01) | |
| *A61Q 19/00* | (2006.01) | |
| *A61Q 19/08* | (2006.01) | |
| *A61K 8/9789* | (2017.01) | |

(52) U.S. Cl.
CPC ......... *A61K 8/9794* (2017.08); *A61K 8/9789* (2017.08); *A61Q 19/00* (2013.01); *A61Q 19/08* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 8,357,382 B1 | 1/2013 | Hilt | |
| 2006/0252949 A1* | 11/2006 | Chordia | C11B 1/104 554/8 |
| 2007/0003536 A1* | 1/2007 | Zimmerman | A61K 8/35 424/94.4 |

FOREIGN PATENT DOCUMENTS

| | | | |
|---|---|---|---|
| WO | WO2012120290 A1 | 9/2012 | |
| WO | WO-2012120290 A2 * | 9/2012 | A61K 8/35 |

OTHER PUBLICATIONS

International Search Report, PCT/US2016/024833 published on Oct. 13, 2016.

* cited by examiner

*Primary Examiner* — Russell G Fiebig
(74) *Attorney, Agent, or Firm* — William J. Davis; Nathalie Tietcheu (57) ABSTRACT

The present invention relates to the cosmetic use of a combination of a hydrolysed rice extract and a grapeseed extract as an active agent to protect cutaneous cells from pollution. The present invention relates also to a cosmetic method of treatment for protecting skin epidermal cells from atmospheric pollution comprising applying on the skin area to be treated a composition comprising a combination of a hydrolysed rice extract and a grapeseed extract.

5 Claims, 4 Drawing Sheets

FIGURE 1

DNA repair: % reduction of cyclobutane pyrimidine dimer (CPD) in NHEK pre and post treated with rice/grapeseed extract of example 1 (Neovixyl) at 1% and 0.5%

FIGURE 2

DNA repair: % reduction of cyclobutane pyrimidine dimer (CPD) in the NHEK pre and post- treated with rice/grapeseed extract of example 1. CPD reduction -dose response

FIGURE 3

Stimulation of wound bed closure of the Organotypic skin treated for 48 h with rice/grapeseed extract of example 1 at 0.5 and 1%

FIGURE 4

DNA damages after ozone exposure. Comet score of NHEK treated with ozone and rice/grapeseed extract of example 1 (Neovixyl)

METHOD OF COSMETIC TREATMENT TO PROTECT THE SKIN FROM POLLUTION AND IMPROVE SKIN REGENERATION

TECHNICAL FIELD

The present invention is in the field of cosmetics and skin care. The invention relates to the use of at least a combination of a hydrolysed rice extract and a grapeseed extract, in a physiologically acceptable medium, for topical application.

The invention relates also to a cosmetic treatment method for protecting the skin from pollution and improving skin regeneration and repair, comprising applying to the skin a composition comprising a combination of a hydrolysed rice extract and a grapeseed extract, in a physiologically acceptable medium.

BACKGROUND

For many years, atmospheric pollution has significantly increased, and became a worldwide environmental problem which has negative impacts on human health and well-being.

It is the outermost tissues like skin, hair, nails and lungs that are initially and directly exposed to harmful pollutants. Thus, the skin is exposed on a daily basis to environmental pollution such as volatile organic compounds, cigarette smoke, ozone, and particulate matter.

Atmospheric pollution is composed of various types of chemical, xenobiotic products and particles. Three major categories of pollutants which may exert harmful effects on exposed tissues are gases, heavy metals and particulates elements.

Atmospheric pollutants can be found both outside, for example due to diesel motor particles, ozone, or heavy metals, and at home, where pollution may be due in particular to solvents released by paints, glues or wallpapers such as toluene, styrene, xylene, benzaldehyde or cigarette smoke.

Among air pollutants, ozone and particle pollution are the most widespread air pollutants and among the most dangerous.

At the ground level, ozone ($O_3$) is formed by the interaction of sunlight on primary pollutants as nitrogen oxides and volatile organic compounds, particularly motor vehicle exhaust emissions.

As ozone is a small molecule and an extremely reactive oxidant, it reacts quickly with the outermost human tissues, noticeably with the respiratory tract and the skin.

More particularly, ozone has been found to lead to toxicological damages (Afaq F. et al. J Invest Dermatol, 2009: 129: 2396-2403.) and to increase DNA damages in normal human epidermal keratinocytes, that will ultimately impair normal cellular function (James T. McCarthy et al. Exp Dermatol, 2013, 22, 358-379).

Repetitive and prolonged exposure to atmospheric pollution acts synergistically with UV exposure to exert negative consequences on skin. This potentially can lead to irritation, inflammation and to increase photodamage and skin aging (Carletto, C. et al. Int J Cosmet Sci. 2000 October; 22(5): 361-70).

Otherwise, it is well known that free radicals play a key role in the aging and photo-aging process, and more particularly in the formation of oxidized, damaged proteins (Harman et al. *J. Gerontol.*, 1956, 11(3), 298-300).

Such external aggressions of the skin by atmospheric pollution can lead to a slow, progressive process of aging which affects all the cutaneous layers of skin and cumulates with chronological aging. The appearance of the skin is modified and one can observed the apparition of wrinkles and fine lines, hyper or hypo-pigmentation blemishes, dryness or even dehydration of the skin, thinning of the epidermis, elastosis, imperfections, age spots. All of these changes affect not only the skin, but also the nails and the hair. These modifications are due, in particular, to a decrease in the functions of cell renewal, and extracellular matrix molecule synthesis, such as collagen, elastin and hyaluronic acid.

Recent avenues of research have been explored to identify active agents capable of fighting environmental stresses (sun, pollution, etc.). These researches have led to the disclosure of numerous more or less effective active agents. As an example, patent application US20070003536 disclosed a method for protecting skin against oxidizing species and oxidative damages of the skin. The method includes applying an admixture of more than ten ingredients selected to combat effects of reactive oxygen and nitrogen species, such as ascorbic acid, SOD, glutathione, grape component, green tea, flavonoid, grapeseed component, green tea component, tocopherol, etc. . . . .

Otherwise, patent application US2002/0192178 disclosed a method for protecting skin against the effects of pollution, comprising applying to the skin a composition comprising an aqueous extract of maize. Patents FR 2915380 and FR 2915383 disclosed a rice peptide extract intended to protect skin from oxidative damages.

However a high demand for cosmetic treatment that protects skin against adverse effects of pollution currently exists. Therefore, it remains important to identify new compounds capable of preventing or protecting skin from atmospheric pollution and improving skin regeneration.

SUMMARY

Provided herein are compositions, cosmetic uses and cosmetic methods to protect efficiently the skin from atmospheric pollution and improve skin regeneration.

A first object of the invention relates to the cosmetic use of a combination of a hydrolysed rice extract and a grapeseed extract, in a physiologically acceptable medium, for topical application. More particularly, a subject of the invention is the cosmetic use of at least a combination of a hydrolysed rice extract and a grapeseed extract, in a physiologically acceptable medium, for protecting the skin from atmospheric pollution and improving skin regeneration and repair.

A second object of the invention relates to a cosmetic treatment method for protecting the skin from atmospheric pollution, comprising applying to the skin a composition comprising a combination of a hydrolysed rice extract and a grapeseed extract, in a physiologically acceptable medium.

A third object of the invention relates to a cosmetic treatment method for improving skin regeneration and repair, comprising applying to the skin a composition comprising a combination of a hydrolysed rice extract and a grapeseed extract, in a physiologically acceptable medium.

A fourth object of the invention relates to a cosmetic treatment method for preventing and/or treating the signs of skin aging and photo-aging due to pollution harmful effects, comprising applying to the skin a composition comprising a combination of a hydrolysed rice extract and a grapeseed extract, in a physiologically acceptable medium.

Accordingly, methods of applying the composition of the invention, to protect the skin from pollution, improve skin regeneration or treat the signs of skin aging and photo-aging due to pollution include topically applying an effective amount of one or more of the various compositions described herein.

DETAILED DESCRIPTION OF THE INVENTION

The object of the invention is to disclose a cosmetic treatment method to protect efficiently the skin from atmospheric pollution, to improve skin regeneration and preventing and/or treating the signs of skin aging and photo-aging due to harmful effects of pollution.

The disclosed methods comprise topically applying to the skin a composition comprising a combination of a hydrolysed rice extract and a grapeseed extract, in a physiologically acceptable medium.

As used herein the term "rice/grapeseed extract" means a combination of a hydrolysed rice extract and a grapeseed extract.

On one hand the rice/grapeseed extract is constituted of hydrolysed rice extract obtained after enzymatic hydrolysis of rice seed flour with vegetal enzymes. To obtain low molecular weight proteins of less than 6 kDa, the mixture is purified using decreasing porosity filters. The hydrolysed rice extract can be obtained according to the process described in U.S. Pat. No. 8,541,374.

The U.S. Pat. No. 8,541,374, claiming the priority of French patent FR0905256 filed Nov. 3, 2009 is incorporated herein by reference.

The term "hydrolysed rice extract" means a mixture of compounds primarily represented by peptides or oligopeptides.

The term "peptides or oligopeptides" means protein fragments composed of a concatenation of at least 2 amino acids linked together by peptide bonds.

Plants from the rice family (Poaceae), in particular those from the genus *Oryza* and more preferably the species *Oryza sativa* L., is used to produce the hydrolysed rice extract of the invention. The plant material used will be either dehulled or not dehulled seed. Preferably, the rice does not undergo prior fermentation.

In a first step, rice is milled using a plant mill. The powder obtained may subsequently be "delipidized" using a conventional organic solvent (for example an alcohol, hexane or acetone).

In a preferred embodiment the plant material is an enriched protein flour product, obtained after rice starch production. To isolate rice starch, the rice proteins are removed from rice flour. The enriched protein flour product is obtained by wet milling, sieving, separation, concentration and drying. The proteins extracted from the rice flour can be resuspended in an alkaline solution.

The soluble fraction containing proteins, glucides and possibly lipids is recovered after the centrifuging and filtration steps. That crude solution is then hydrolysed under managed conditions to generate soluble peptides.

In accordance with the invention, the hydrolysis is carried out using proteolytic enzymes and preferably using endoproteases of plant origin (papain, bromelain, ficin) and from micro-organisms (*Aspergillus, Rhizopus, Bacillus*, etc).

The hydrolysed rice extract obtained at this stage may be purified further in order to select the low molecular weight fractions, preferably less than 6 kDa. Purification may advantageously be carried out by successive ultrafiltration steps through filters with decreasing porosities, collecting the filtrates at each step, and/or by a method of the chromatographic type, in order to specifically enrich the hydrolysate in peptides.

The filtrate is then diluted at a concentration between 20 g/Kg and 40 g/Kg, preferably at 30 g/Kg of dry matter with solvents, such as water, glycerol, ethanol, propanediol, butylene glycol, dipropylene glycol, ethoxylated or propoxylated glycols, cyclic polyols or any mixture of these solvents. Advantageously, the solvent can be a mixture of 30% glycerol and 0.5% sodium benzoate in water.

Then, optionally, the diluted active agent is sterilized by sterile filtration and pasteurized for example for one night in the oven at 65° C.

Next, a dilution in water or in any mixture containing water is carried out, followed by sterilization by ultra filtration in order to obtain a rice hydrolysed extract characterized by a protein content ranging from 10 to 20 g/l.

The hydrolysed rice extract obtained in accordance with the invention is characterized qualitatively and quantitatively by high performance size exclusion chromatography (SEC HPLC) using a high pressure liquid chromatography (HPLC), equipped with a size exclusion analytical column which can analyse proteins and peptides with molecular weights between 0.2 to 10 kDa (using an appropriate solvent gradient).

HPLC analysis shows that the hydrolysed rice extract obtained is composed of peptides with a molecular weight of less than 6 kDa.

On another hand the rice/grapeseed extract is composed of grapeseed extract (botanical species *Vitis vinifera*).

The grapeseed extract is obtained after extraction of grapeseed cake (oil grapeseed extraction by-product) in water, at pH between 4 and 7 advantageously in presence of activated charcoal. The mixture is then purified using decreasing porosity filters.

Acid washed activated carbon is advantageously used for decolourization and purification, where the use of high purity extract is required.

Then hydrolysed rice extract and grapeseed extract are mixed in a ratio ranging from 5 to 9 of hydrolysed rice extract and ranging from 5 to 1 of grapeseed extract. Preferably, the combination is prepared by mixing 9 parts in weight of hydrolysed rice extract and 1 part in weight of grapeseed extract. In that way, the ratio is adjusted at 9:1 (w/w) respectively in hydrolysed rice extract and grapeseed extract. Then the protein content is adjusted between 10 and 20 g/Kg, preferably 15 g/Kg, by dilution in water. Preferably, the dilution is made in a mixture of water and glycerol in order to obtain a final concentration of 30% of glycerol.

A preservative such as sodium benzoate at 0.5% can be added. The final solution is then filtered under sterile atmosphere and pasteurized at low temperature 8 hours at 65° C.

In a preferred embodiment; the final product obtained has a pH ranging from 4.0 to 5.0, a density at 20° C. ranging from 1.06 to 1.09 g/cm3, a refractive index at 20° C. ranging from 1.360 to 1.390 and a protein content ranging from 10.0 to 20.0 g/kg (as measured by Lowry assay). A preservative are sodium benzoate at the concentration from 0.45 to 0.55% can be added.

Without being bound to any scientific theory, inventors have now discovered that a rice/grapeseed extract is capable of protecting the skin from pollution and improving skin regeneration, and is further useful for preventing and/or treating the signs of skin aging and photo-aging due to pollution harmful effects.

The rice/grapeseed extract according to the invention was tested and it demonstrated biological effects on the keratinocytes and the fibroblasts of the skin. It was further demonstrated that the rice/grapeseed extract acted as protector against DNA damage caused to the cutaneous cells by ozone.

It was also demonstrated that the rice/grapeseed extract accelerated the skin regeneration and skin repair in an ex vivo wound healing model.

The protective potential of rice/grapeseed extract of the invention was evaluated against ozone-induced oxidative stress. The rice/grapeseed extract of the invention dramatically reduced the oxidative responses during ozone exposure and was therefore found as very effective to protect the cutaneous cells from DNA damages.

In a first aspect, the present invention concerns the cosmetic use of a rice/grapeseed extract, as an active agent, in a physiologically acceptable medium, for topical application.

In a preferred embodiment, the invention relates to the cosmetic use of at least a rice/grapeseed extract, in a physiologically acceptable medium, as an active agent for protecting the skin from pollution and improving skin regeneration in a composition for topical application.

In a more preferred embodiment, the invention relates to the cosmetic use of a rice/grapeseed extract as an active agent wherein the hydrolysed rice extract and grapeseed extract are mixed in a ratio ranging from 5 to 9 of hydrolysed rice extract and ranging from 5 to 1 of grapeseed extract. Preferably, the ratio is adjusted at 9:1 (w/w) respectively in hydrolysed rice extract and grapeseed extract.

In another preferred embodiment, the composition comprises 0.01 to 5% of rice/grapeseed extract, and preferably 0.5% to 2% wherein the hydrolysed rice extract is obtained after enzymatic hydrolysis with vegetal enzymes to obtain low molecular weight proteins (less than 6 kDa). The hydrolysed rice extract is purified using decreasing porosity filters. The grapeseed extract is obtained after extraction of grapeseed cake (grapeseed oil extraction by-product) in water at pH between 4 and 7. The mixture is purified using decreasing porosity filters. Then hydrolysed rice extract and grapeseed extract are mixed in a ratio ranging from 5 to 9 of hydrolysed rice extract and from 5 to 1 of grapeseed extract. Preferably the ratio is 9:1 respectively of hydrolysed rice extract and grapeseed extract. The rice/grapeseed extract represents 70% of the final product. glycerol (30%) are added. Optionally sodium benzoate at 0.5% might be added. The final solution is then filtered under sterile atmosphere and sterilized by low temperature pasteurization.

The expression "Topical application" is understood to be the application or spreading of a composition containing said rice/grapeseed extract, on the surface of the skin or a mucous membrane.

The composition comprises 0.5% to 2% of said rice/grapeseed extract must be understood as the weight of rice/grapeseed extract compared to the total weight of the composition.

The range of 0.5% to 2% % must be understood as the "effective amount" of active agent in the composition described herein.

The expression "effective amount" means herein an amount such as the protection against atmospheric pollution is ensured.

The expression "active agent for protecting the skin from pollution and improving skin regeneration" is understood to refer to any rice/grapeseed extract that may protect the cells from DNA damages after ozone exposure and accelerate cutaneous regeneration.

In a second aspect, the present invention concerns a cosmetic treatment method for protecting skin epidermal cells from atmospheric pollution, comprising topically applying to the skin to be treated a cosmetic composition wherein the composition comprises 0.01 to 5% of an active ingredient consisting of a combination of a hydrolysed rice extract and a grapeseed extract (rice/grapeseed extract) in a ratio of 9:1 and a physiologically acceptable medium.

In preferred embodiment the cosmetic composition comprises 0.5% to 2% of the active ingredient rice/grapeseed extract.

In another embodiment the cosmetic treatment method comprises the following steps:
  a. obtaining hydrolysed rice extract by enzymatic hydrolysis with vegetal enzymes to obtain low molecular weight peptides of molecular weight less than 6 kDa,
  b. purifying the hydrolysed rice extract using decreasing porosity filters,
  c. obtaining the grapeseed extract from grapeseed cake in water at a pH between 4 and 7,
  d. purifying the grapeseed extract using decreasing porosity filters; and
  e. combining the extracts obtained at step b and d in a ratio ranging from 5 to 9 of hydrolysed rice extract and from 5 to 1 of grapeseed extract, preferably in a ratio of 9:1 to represent 70% of the final product,
  f. glycerol is then added in the product obtained at step f to represent 30% of the final product,
  g. Optionally sodium benzoate at 0.5% might be added. The final solution is then filtered under sterile atmosphere and sterilized by low temperature pasteurization.

In a preferred embodiment the active ingredient rice/grapeseed extract comprises a protein content ranging between 10 and 20 g/Kg, and more preferably a protein content of 15 g/Kg.

In a preferred embodiment the active ingredient rice/grapeseed extract comprises hydrolysed rice extract composed of peptides with a molecular weight of less than 6 kDa.

In a third aspect, the present invention concerns a cosmetic treatment method for improving skin regeneration and repair comprising topically applying to the skin to be treated a cosmetic composition wherein the composition comprises from 0.01 to 5% and more preferably from 0.5% to 2% of the active ingredient rice/grapeseed extract.

In a fourth aspect, the present invention concerns a cosmetic treatment for preventing and/or treating the signs of skin aging and photo-aging due to pollution harmful effects, comprising topically applying to the skin to be treated a cosmetic wherein the composition comprises from 0.01 to 5% and more preferably from 0.5% to 2% of the active ingredient rice/grapeseed extract.

The expression "photo-aging" according to the invention denotes premature skin aging caused by prolonged and cumulative exposure to the sun.

The expression "signs of skin aging and photo-aging" include but are not limited to any manifestation which is visible on the skin caused by aging and by acute or chronic exposure to external stresses such as UV radiation. This in particular means wrinkles, deep and coarse wrinkles, fine lines, cracks, slackening of cutaneous and sub-cutaneous tissues, the loss of skin elasticity and atony, loss of firmness and tonus, and dermal atrophy. Furthermore, the term "signs of skin aging and photo-aging" means enlarged pores, imperfections, discoloration, age spots, keratosis, loss of collagen, and other changes in the dermis and epidermis, but also any modification to the external appearance of the skin, the nails and the hair due to aging and photo-aging such as, for example, superficial roughness of the stratum corneum, but also any internal modification to the skin which does not systematically result in a modified external appearance, such as thinning of the skin.

According to another advantageous embodiment, the rice/grapeseed extract is dissolved in a cosmetic or pharmaceutical vector such as liposomes or microcapsule or nanocapsule or adsorbed onto powdered organic polymers, mineral supports such as talc or bentonite, and more generally dissolved in or fixed onto any physiologically acceptable vector.

The compositions of the present invention can be applied in any appropriate manner, in particular orally or topically, and the formulation of the compositions will be adapted by the person skilled in the art, in particular for cosmetic or dermatological compositions. The compositions of the present invention are advantageously designed to be administered topically. These compositions must therefore contain a physiologically acceptable medium, i.e. compatible with the skin and epithelial appendages, and cover all cosmetic or dermatological forms.

The term "physiologically acceptable medium" means media which is suitable for contacting with human skin or the nails or the hair, with no risk of toxicity, incompatibility, instability, allergic response or the like.

Preferably, said rice/grapeseed extract is present in the composition as an active ingredient in a quantity representing approximately 0.01% and 5% relative to the total weight of the final composition and most preferably in a quantity representing 0.05% to 2% of the total composition weight.

The compositions of the present invention may be in the form of an aqueous, hydro-alcoholic or oily solution; oil-in-water emulsion, water-in-oil emulsion or multiple emulsions; these can also exist in the form of creams, suspensions or even powders adapted for application on the skin, mucus membranes, lips and/or epithelial appendages. These compositions can also be more or less fluid and have the appearance of a cream, a lotion, milk, a serum, pomade, a gel, a paste or a mousse. They can also exist in solid form, as a stick, or can be applied to the skin as an aerosol. They can also be used as a skincare product and/or as a makeup product.

Furthermore, the composition comprises any conventionally used additive envisaged in the scope of application as well as necessary additives for their formulation, such as co-solvents (ethanol, glycerol, benzyl alcohol, damper . . . ), thickeners, thinners, emulsifiers, antioxidants, colorants, solar filters, pigments, fillers, preservatives, perfumes, odor absorbers, essential oils, oligoelements, essential fatty acids, surfactants, film-forming polymers, chemical filters or minerals, moisturizing agents or thermal waters etc. Water-soluble, preferably natural, polymers, such as polysaccharides or polypeptides, cellulose derivatives of the type methylcellulose or hydroxypropylcellulose, or even synthetic polymers, poloxamers, carbomers, siloxanes, PVA or PVP, and in particular polymers sold by the company Ashland, can be cited, for example.

In all cases, the skilled person will ensure that these adjuvants as well as their proportions are selected so that they do not have a deleterious effect on the desired advantageous properties of the composition of the invention. These adjuvants may, for example, be present in concentrations of 0.01% to 20% of the total composition weight. When the composition of the invention is an emulsion, the fatty phase may represent 5% to 80% by weight, preferably 5% to 50% by weight with respect to the total composition weight. The emulsifiers and co-emulsifiers used in the composition will be selected from those in conventional use in the field under consideration. As an example, they may be used in a proportion of 0.3% to 30% by weight, with respect to the total composition weight.

In a particular embodiment, the composition of the present invention further contains at least one other active principle promoting the action of said rice/grapeseed extract. As other active principle, the following types of ingredients can be cited, in a non-limiting manner: other peptide active agents, vegetable extracts, healing agents, anti-aging agents, anti-wrinkle agents, soothing agents, anti-free radicals, anti-ultraviolet radiation agents, agents for stimulating dermal macromolecular synthesis or energetic metabolism, moisturizing agents, antibacterial agents, antifungal agents, anti-inflammatories, anesthetics, agents modulating cutaneous differentiation, cutaneous pigmentation or depigmentation, and agents for stimulating nail and hair growth.

It is preferable for an anti-free radical or antioxidant agent, or an agent stimulating dermal macromolecular synthesis or energetic metabolism, to be used.

In a more specific embodiment, the composition according to the invention will comprise, in addition to the rice/grapeseed extract according to the invention:

sunscreens, ultraviolet and Infrared screens
anti-free radical agents,
DHEA (dehydroepiandrosterone),
at least one cytochrome c-activating compound, and/or;
at least one aquaporin-activating compound and/or;
at least one sirtuin-activating compound and/or;
at least one compound that increases cell adhesion and/or;
at least one compound that increases the production of matrix proteins of the collagen or laminin type, etc.;
at least one HSP protein-modulating compound;
at least one compound that increases cell energy;
at least one pigmentation-modulating compound such as a yeast, amaranth, linseed, bean, cacao, corn, soy, sunflower, rapeseed or pea peptide extract;
at least one compound improving the skin barrier function;
at least one mitochondria-protecting compound.
vitamin A and notably retinoic acid, retinol, retinol propionate, retinol palmitate,
vitamin B3 and notably niacinamide, niconitate of tocopherol,
vitamin B5, vitamin B6, vitamin B12, panthenol, vitamin C, and notably ascorbic acid, ascorbyl glucoside, ascorbyl tetrapalmitate, magnesium and sodium ascorbyl phosphate, vitamins E, F, H, K, PP, and coenzyme Q10, metalloproteinase inhibitor, activator of Tissue Inhibitor Metalloproteinase (TIMP), aminoacids and notably arginine, ornithine, hydroxyproline, hydroxyproline dipalmitate, palmitoylglycine, hydroxylysine, methionine and its derivatives, N-acylated aminoacids, natural or synthetic peptides, including, di-, tri-, tetra-, penta- and hexapeptides and their lipophilic derivatives, isomers and complex with other molecules such as metallic ion (i.e. copper, zinc, manganese, magnesium, and others), peptides sold under commercial names MATRIXYL®, ARGIRELINE®, COL-LAXYL™, PEPTIDE VINCI 02™, CHRONOGEN™, LAMINIXYL IS™, PEPTIDE Q10™ peptidic plant extracts obtained by hydrolysis or any other methods such as soy extract, einkorn extract, rapeseed extract, flaxseed extract, corn extract, or pea extract, carob extract, bean extract, fava extract, yeast extract, artemia salina extract, dehydroacetic acid (DHA), natural or synthetic phystosterols, alpha- and beta-hydroxyacids, silanols, sugar amines, glucosamine, D-glucosamine, N-acetyl-glucosamine, N-acetyl-D-glucosamine, mannosamine, N-acetyl mannosamine, galactosamine, N-acetyl galactosamine, polyphenols, isoflavones, flavonoids, such as grap extract, pine extract, olive extract, lipids such as ceramides or phospholipids, animal oils such as squalenes or squalanes, vegetal oils, such as almond oil, coconut oil, castor oil, jojoba oil, olive oil, rapeseed oil, peanut oil, sunflower oil, wheat germ oil, corn germ oil, soybean oil, cotton oil, alfalfa oil, poppy oil, pumpkin seed oil, evening primrose oil, millet oil, barley oil, rye oil, safflower oil, passion oil, hazelnut oil, palm oil, apricot kernel oil, avocado oil, calendula oil, ethoxylated vegetable oils, or shea butter, The abovementioned compounds can be natural, such as peptide hydrolysates of plants, or also synthetic, such as peptide compounds.

The following examples describe and demonstrate the efficiency of rice/grapeseed extract as described in accordance with the invention but should not be interpreted as limiting the scope of the present invention.

Example 1: Preparation of Rice/Grapeseed Extract

A—Preparation of the Hydrolysed Rice Extract (Species *Oryza sativa* L):

In a first step, 42 g of rice flour enriched at 80% in proteins (obtained after rice starch production) are suspended in 1 kg of water kept under agitation. Then proteases Alcalase® at 0.04% w/w and bromelain at 0.04% w/w are added for 2 hours at 55° C., pH is adjusted at a range of pH 7.0 to 7.5.

Enzymes are then deactivated 2 hours at 80° C. The pH is then adjusted at a value ranging from 4.3 to 4.7.

The extract is clarified by centrifugation at 4000 rpm, 10 min, then the supernatant is successively filtered through membranes of decreasing porosity from 500 μm for clarification to 0.2 μm for sterilization.

The hydrolysed rice extract is then ultrafiltrated on a Millipore Helicon filtration cartridge (cutoff 6 kDa). The high molecular weight compounds contained in the retentate are removed and the filtrate is collected. This filtrate represents a raw form of the socalled hydrolysed rice extract. After analysis, particularly by HPLC, it is observed that the extract contains approximately 80% of peptides with a molecular weight of less than 6 kDa.

At this stage, approximately 700 grams of extract are obtained containing:

Proteins and low molecular weight peptides: 77%
Carbohydrates: 13%
Amino-acids 6.3%
Polyphenols: 1.6%
Ash: 2.1%

To be stored for a latter use, the hydrolysed rice extract is added with 30% glycerol and 0.5 w/w sodium benzoate.

Extract is then sterilized by 0.22 μm filtration and finally pasteurized in a oven overnight at 65 C At this step, the hydrolysed rice extract is under the form of a slight yellow solution, containing from 32 g/l of dry extract and the concentration of peptide compounds determined by the Lowry method is 17 g/l.

B—Preparation of the Grapeseed Extract (Species *Vitis vinifera*):

Grape seed cake flour at 10% w/w is suspended en water in presence of activated charcoal (Norit SX Plus®) at 5 g/kg and left 1 hour at 50° C.

Then 10 g/Kg of Diatomaceous Earth (filtrating agent) is added in order to improve filtration yields.

Extract is then filtered using depth filter media. Successive filtrations are performed in order to purify the product from clarification (500 μm) to sterilization (0.2 μm).

To be stored for a latter use, the grapeseed extract is then diluted by the addition of 30% glycerol and 0.5% sodium benzoate. The extract then obtained is composed of 0.5% dry matter which is composed of 95% sugars, 4.5% proteins and 0.5% polyphenols.

C—Preparation of the Combination of the Hydrolysed Rice Extract and the Grape Seed Extract.

Extracts are mixed at a ratio of 9 parts (weight) of rice hydrolysed extract obtained at the step A et 1 part (weight) of grapeseed extract obtained at the step B. The mix is then diluted in water and glycerol in order to be standardized at a concentration of protein (low molecular weight peptides) of 15 g/Kg, and a concentration of 0.5% sodium benzoate and 30% glycerol.

Final filtration is performed on a 0.22 μm polyethersulfone membrane. The product is then pasteurized by low temperature overnight at 65° C.

The final product obtained has a pH of 4.5, a density at 20° of 1.07 g/cm3, a refractive index at 20° C. of 1.370 and a protein content of 15 g/Kg (as measured by Lowry assay). Preservative is sodium benzoate at the concentration of 0.5%.

Example 2: Reduction of Pyrimidines, Cyclobutane Pyrimidine Dimer (CPD) in the NHEK Pre and Post-Treated with Rice/Grapeseed Extract of Example 1

Cells NHEK were irradiated with UVB and incubated for 18 h post irradiation to allow cells to repair DNA photolesions. Cellular DNA absorbs UV light efficiently around 260 nm, leading to the formation of dimeric photolesions between adjacent pyrimidines, cyclobutane pyrimidine dimer (CPD)

The NHEK were pretreated with rice/grapeseed extract of example 1 for 24 h prior the UVB irradiation at 100 J/m2. The treatment with corresponding concentration of active was extended post irradiation. The cells were collected 18 h post irradiation, the DNA isolated, and CPD detected by Elisa.

Materials:
DNeasy Tissue Kit—Qiagen, cat#69504
NHEK, p3
EpiLife—Cascade, cat#M-EPI-500-CA,
Human Keratinocyte Growth Supplement, cat# S-001-5
Trypsin/EDTA Solution—Cascade, cat#R-001-100,
Ethanol—EM Science, cat# AX0441-3,
RNase A—Qiagen, cat# R6513,
Lambda DNA—New England BioLabs, cat# N3011L (for standards)
Anti-CPD Cosmos USA Ab—TDM-2cat#D194;
Anti-Mouse Termo scientific cat#31432 (stock at 0.4 mg/ml)
ELISA 10× wash buffer; ImmunoChemistry cat#652
ELISA 5× coating buffer ImmunoChemistry cat#646
Qiagen Blood and tissue kit cat#69506
Quanta Blue Flurogenic substrate 15169 Lot#IG113044

Procedure:
Grow NHEK to 60-70% confluence in T75 plates p-2
Wash cells with PBS and trypsinize the cells
Count the cells and plate $1 \times 10^5$ per p50
Treat with rice/grapeseed extract of example 1 (also referred as Neovixyl) at following final dilutions at 1; 2; 1; 0.5; 0.1 and 0.01% v/v in medium)

After the treatment (24 h) rinse plate and add 5 ml PBS
Irradiate samples with an UV irradiation chamber at 0.01 $J/cm^2$
Replace PBS with medium with corresponding actives and return into the incubator for 20 h. Scrape cells in the PBS and spin down and freeze the pellet Isolation of DNA from samples by using DNeasy kit from Qiagen following manufacturer instructions. Samples were treated with appropriate concentration of DNAse free RNAse (Add 4 µl RNAse A (100 µg/µl) to cell suspension and incubate for 5 min at room temp). Measure and calculate final concentration of DNA. The reproducible results were obtained using DNA in the range between 50 ng/well. Calculate appropriate DNA enough for the 4 wells and resuspend in TE buffer (final volume 200 µl) in silicon tubes. Denature the DNA by boiling secured tubes for 10-15 min, and then chill rapidly by transferring tubes in an ice bath for at least 15-30 min.

Add 200 µl of 2× coating buffer and mix the sample by inverting the tubes
Apply 100 µl of the coating mixture in the Elisa well in triplicates
Dry plates overnight at 37° C. (do not cover the plates)
Preparation of plates for detection of CPD (all subsequent incubations are done on orbital shaker at RT)
Wash plates 2×10 min with Elisa 1× washing buffer
Block with 150 µl Neptune blocking buffer for 1 h at RT
Preparation of primary antibody dilutions
Dilute anti CPD antibody (TDM-2) in 1× washing buffer for final concentration of 1:12000
Apply 100 µl of the primary antibody and incubate plates in RT for 60 min
Wash 3×10 min with a 180 µl of washing buffer each
Preparation of secondary antibody and substrate
After washing add 100 µl of diluted secondary antibody and incubate on RT for 1 h. (in 1× washing buffer to achieve final dilution of 1:10000)
Wash 3×5 min with 180 µl of washing buffer
Wash with 1×3 min with PBS
Apply 100 µl of substrate into wells (substrate—45 ml of part 1 and 5 ml of part 2; to achieve 9:1)
Read on Elisa reader 320/405 immediately and every 10 min for up to 1 h Results:
In Table 1 and 2, the rice/grapeseed extract of example 1 is called Neovixyl.

TABLE 1 treatments of keratinocytes

| | UVB | natural repair | Neovixyl 2% | Neovixyl 1% | Neovixyl 0.5% | Neovixyl 0.1% | Neovixyl 0.01% |
|---|---|---|---|---|---|---|---|
| Sample set 1 | 2606 | 2170 | 1590 | 1578 | 1879 | 1805 | 2288 |
| | 2214 | 1876 | 1628 | 1455 | 1544 | 1756 | 2200 |
| | 2771 | 2167 | 1682 | 1469 | 1382 | 2023 | 2374 |
| Sample set 2 | 2902 | 2048 | 2037 | 1637 | 1799 | 2307 | 1617 |
| | 2822 | 1910 | 1692 | 1597 | 1834 | 2353 | 1576 |
| | 2738 | 2030 | 1797 | 1783 | 1877 | 2255 | 1797 |
| Average | 2675 | 2034 | 1738 | 1587 | 1719 | 2083 | 1975 |
| Mean | 2755 | 2039 | 1687 | 1588 | 1816 | 2139 | 1998 |
| STD | 247 | 124 | 163 | 120 | 207 | 261 | 354 |
| SE | 82 | 41 | 54 | 40 | 69 | 87 | 118 |
| % | | 24 | 35 | 41 | 36 | 22 | 26 |
| % from the untreated beyond natural repair | | | 11 | 17 | 12 | −2 | 2 |

TABLE 2 treatments of keratinocytes

| | UVB | natural repair | Neovixyl 1% | Neovixyl 0.5% |
|---|---|---|---|---|
| Sample set 1 | 4707 | 3040 | 1354 | 1353 |
| | 4920 | 2990 | 1459 | 1490 |
| | 5591 | 2984 | 1491 | 1491 |
| Sample set 2 | 5464 | 3181 | 2122 | 2242 |
| | 5155 | 3220 | 2157 | 2105 |
| | 5187 | 1914 | 1938 | 2238 |
| Sample set 3 | | 1691 | 1820 | 1882 |
| | | 1566 | 1560 | 1959 |
| | | 1655 | 1779 | 1907 |
| Average | 5171 | 2471 | 1742 | 1852 |
| Mean | 5171 | 2984 | 1779 | 1907 |
| STD | 329 | 735 | 293 | 334 |
| SE | 110 | 245 | 98 | 111 |
| % | | 52 | 66 | 64 |
| % from the untreated beyond natural repair | | | 14 | 12 |

Figure 1:
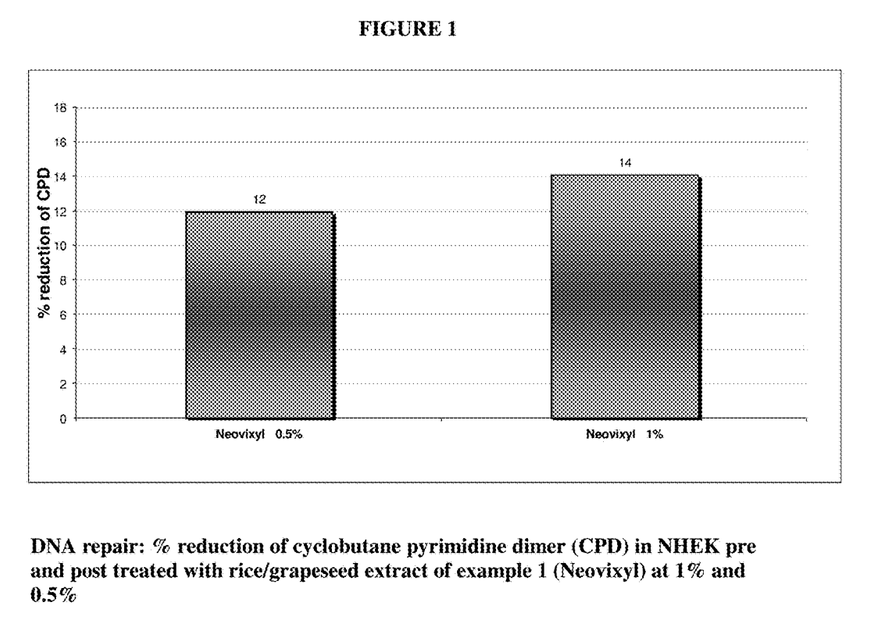
FIG. 1 represents: DNA repair: % reduction of pyrimidines, cyclobutane pyrimidine dimer (CPD) in NHEK pre and post treated with rice/grapeseed extract of example 1 (Neovixyl) at 1% and 0.5%.

Two experiments were done regarding the evaluation of CPD repair in NHEK. In the first, treatment of NHEK with rice/grapeseed extract of example 1 demonstrates increase of CPD repair (FIG. 1). The reduction of CPD was at 12-14%. In the second experiment, the effective dose of rice/grapeseed extract of example 1 was evaluated in the range of 0.01-2% and again the maximum CPD reduction was seen in NHEK treated with 1% rice/grapeseed extract of example 1 (FIG. 2).

Figure 2:
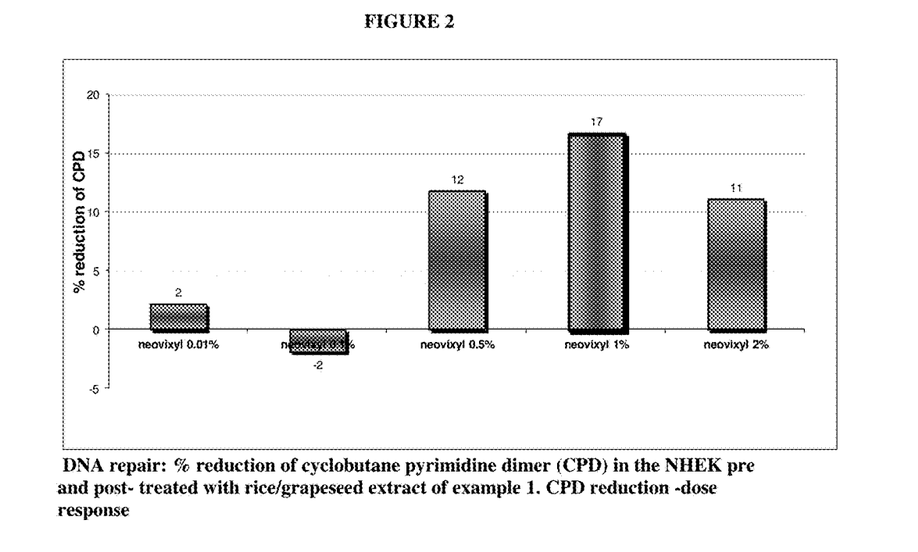
FIG. 2 represents: DNA repair: % reduction of pyrimidines, cyclobutane pyrimidine dimer (CPD) in the NHEK pre and post-treated with rice/grapeseed extract of example 1 ((Neovixyl). CPD reduction-dose response.

In FIGS. 1 and 2, rice/grapeseed extract of example 1 is called Neovixyl (NEOVIXYL™).

Example 3: Stimulation of Wound Bed Closure of the Organotypic Skin Treated for 48 h with Rice/Grapeseed Extract of Example 1 at 0.5 and 1%

Procedure of Wound Healing Test

Migration of the cells is regulated by extracellular matrix, soluble factors as well as intercellular interactions. The effect of these factors can be studied by using wound healing method. Organotypic skins were wounded using a hand held scalper at approximately 2 mm wide strip, without disturbance of the dermal compartment. An aliquot of rice/grapeseed extract of example 1 diluted in PBS was added to the wound site and then incubated for 48 h. The corresponding concentration of rice/grapeseed extract of example 1 was added to the incubation medium underneath as well. The organotypic skin were fixed in buffered formaline and process by standard histological procedures by McClain laboratory. The images of the organotypic skin wound bed were taken using Olympus microscope at 40 and 100× with Nikon digital camera DS-R1. The length from the wound base, to the tip of the migrating keratinocytes was measured using Nikon Elements BR-3-10 program. The distances from both sides of the wound edges were added and data presented in length ($\mu$m) and % of the increase in comparison to the untreated wound.

Results

In Table 3, the rice/grapeseed extract of example 1 is called Neovixyl

TABLE 3

| | Total length- $\mu$m | % increase from untreated |
|---|---|---|
| Untreated | 661.0 | / |
| Neovixyl 0.5% | 790.8 | 19.6 |
| Neovixyl 1% | 782.2 | 18.3 |

Figure 3:
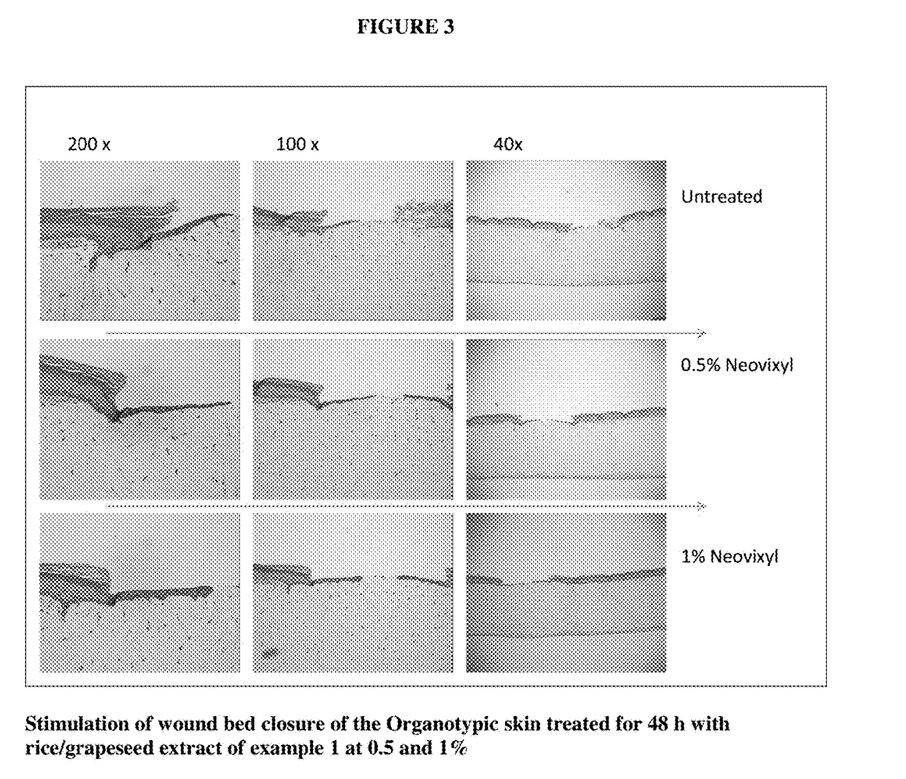
FIG. 3 represents the stimulation of wound bed closure of the Organotypic skin treated for 48 h with rice/grapeseed extract of example 1 (Neovixyl) at 0.5 and 1%.

Results are shown in FIG. 3, wherein rice/grapeseed extract of example 1 is called Neovixyl (NEOVIXYL™)

Example 4: Assessment of Ozone Induced DNA Fragmentation by Comet Assay after Treatment with Rice/Grapeseed Extract of Example 1

Protocol
Tissue Culture

Normal Human Epidermal Keratinocytes (NHEK) were sub-cultivated on 60 mm Petri dishes until reaching approximately 50% confluency. Rice/grapeseed extract of example 1 was prepared in NHEK media at the following concentrations: 0.1%, 0.5% and 1%. NHEK were then treated either with fresh media or media containing rice/grapeseed extract of example 1 and incubated overnight.

Ozone Treatment

Prior to ozone exposure, the cell culture media were removed and replaced with 2 ml of Dulbecco's Phosphate Buffered Saline. The plates were placed in an ozone chamber with a rotating stage set at a 450 angle. Cells were then exposed to 0.4 ppm ozone for 20 minutes, followed by re-incubation with their respective media for 2 hours, and harvested by treatment with trypsin. Lastly, the cells were counted and 1×104 cells were used for the Comet assay.

Comet Assay

NHEK were trypsinized, washed with PBS and suspended in PBS at 1×105 cells/mL. Cells were then dispersed in melted agarose (Trevigen, cat#4250-050-02) at 37° C. at a 1:10 ratio. 75 $\mu$l of the cell/agarose mixture was pipetted evenly on to each spot of the comet slide (Trevigen, cat#4250-050-03) and then incubated at 4° C. for 10 minutes. Slides were immersed in cold lysis solution (Trevigen, cat#4250-050-01) on ice for 3 hours. Slides were removed from the lysis solution and placed into an alkaline solution (300 mM NaOH, 1 mM EDTA, pH>13) at room temperature for 30 minutes. Then the slides were placed in an electrophoresis apparatus chilled in ice so that they were equidistant from the electrodes. Cold alkaline electrophoresis solution (300 mM NaOH, 1 mM EDTA, pH>13) was poured into the apparatus so that it just covered the slides. Electophoresis ran for 30 minutes at 23V. After electrophoresis the slides were rinsed in $H_2O$ and immersed in 70% EtOH for 5 min. Slides were removed from the EtOh solution and placed on a towel to air dry overnight. SYBR green (Trevigen, cat#4250-050-05) was diluted in TE buffer (10 mM Tris-HCl, 1 mM EDTA, pH 7.5) 1:10000. 50 $\mu$l of diluted SYBR green was pipetted on to each spot. Slides were incubated at 4° C. for 5 min. Then slides were allowed to dry again after removing excess SYBR green from the slides. Slides were viewed under an Olympus BX51 microscope with the FITC filter with the 20× objective. Images were captured using the Nikon Elements software. The tail moments were determined with the Comet Score software from Tri Tek.

Results

Figure 4:
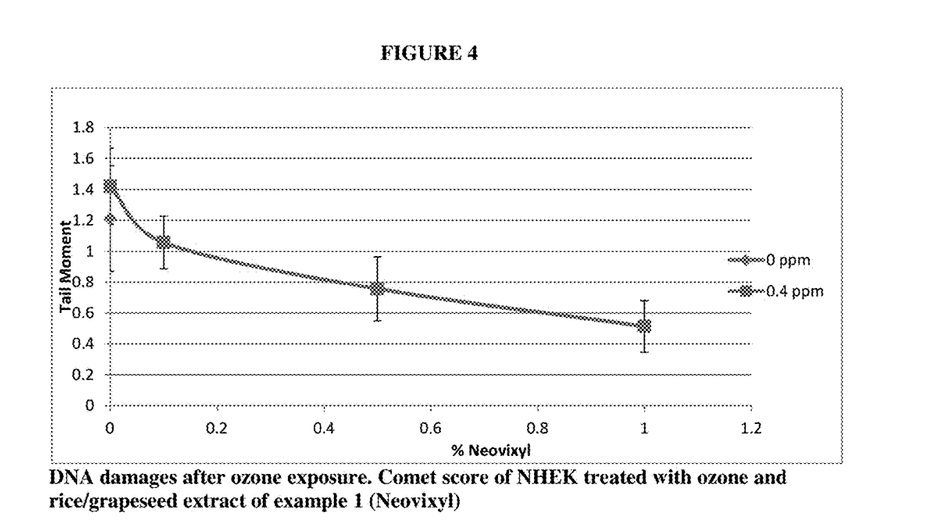
FIG. 4 represents DNA damages after ozone exposure. Comet score of NHEK treated with ozone and rice/grapeseed extract of example 1 (Neovixyl).

FIG. 4 represents DNA damages after ozone exposure. Comet score of NHEK treated with ozone and rice/grapeseed extract of example 1, wherein rice/grapeseed extract of example 1 is called Neovixyl (NEOVIXYL™).

CONCLUSIONS

Rice/grapeseed extract of example 1 was able to counteract the ozone induced increase in DNA fragmentation. Treatment with rice/grapeseed extract of example 1 protects the cells against the effects of ozone.

What is claimed is:

1. A cosmetic treatment method for protecting skin epidermal cells from DNA damages induced by ozone exposure and UVB irradiation, comprising topically applying to skin in need thereof an effective amount of a cosmetic composition wherein the composition comprises 0.5 to 2% of an active ingredient consisting of a combination of a hydrolysed rice extract and a grapeseed extract in a ratio adjusted at 9:1 (w/w) and a physiologically acceptable medium, wherein the process to prepare the active ingredient comprises the following steps:
   a. obtaining hydrolysed rice extract by enzymatic hydrolysis with vegetal enzymes, said hydrolysed rice extract is consisting of low molecular weight peptides of molecular weight less than 6 kDa, b. purifying the hydrolysed rice extract using decreasing porosity filters;
c. obtaining the grapeseed extract from grapeseed cake in water at a pH between 4 and 7,
d. purifying the grapeseed extract using decreasing porosity filters; and
e. combining the extracts obtained at step b and d in a weight ratio of 9:1
f. adding 30% of glycerol in 70% of the product obtained at step e to prepare the active ingredient
g. using the active ingredient obtained at step f to prepare a cosmetic composition comprising the active ingredient at a weight ratio of 0.5 to 2% of the cosmetic composition.

2. The cosmetic treatment method of claim 1, wherein the combination of a hydrolysed rice extract and a grapeseed extract comprises a protein content ranging between 10 and 20 g/Kg, and more preferably a protein content of 15 g/Kg.

3. The cosmetic treatment method of claim 1, wherein the hydrolysed rice extract is consisting of peptides with a molecular weight of less than 6 kDa.

4. The cosmetic treatment method of claim 1, wherein the method is used to improve skin regeneration and repair.

5. The cosmetic treatment method of claim 1, wherein the method is used for preventing and/or treating the signs of skin aging and photo-aging due to pollution harmful effects.

* * * * *

UNITED STATES PATENT AND TRADEMARK OFFICE
CERTIFICATE OF CORRECTION

| | | |
|---|---|---|
| PATENT NO. | : 10,478,393 B2 | Page 1 of 1 |
| APPLICATION NO. | : 15/564806 | |
| DATED | : November 19, 2019 | |
| INVENTOR(S) | : Frederique Portolan et al. | |

It is certified that error appears in the above-identified patent and that said Letters Patent is hereby corrected as shown below:

On the Title Page

Item (72) Inventors at Column 1:
Delete the name of the 8 inventor "Nadine A. PERDONET"
Insert the correct name -- Nadine A. PERNODET --

Signed and Sealed this
Twelfth Day of May, 2020

Andrei Iancu
*Director of the United States Patent and Trademark Office*